US006228886B1

(12) United States Patent
Anderson et al.

(10) Patent No.: US 6,228,886 B1
(45) Date of Patent: *May 8, 2001

(54) NUTRITIONAL FORMULATIONS CONTAINING WATER-MISCIBLE LIPID DERIVATIVES AS ANTIBACTERIAL AGENTS

(75) Inventors: Steven N. Anderson, Aurora, IL (US); Milo Duane Hilty, Lewis Center, OH (US); Terry Bruce Mazer, Reynoldsburg, OH (US); Joseph Schaller, Columbus, OH (US); Melinda Guzman-Harty, Gahanna, OH (US); Theresa Siu-Ling Wai Lee; Lisa Ann Reaves, both of Columbus, OH (US); Jin-Zhou Liu, Westerville, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/577,423

(22) Filed: May 22, 2000

Related U.S. Application Data

(63) Continuation of application No. 09/306,608, filed on Apr. 16, 1999, now Pat. No. 6,066,669, which is a continuation of application No. 08/690,737, filed on Jul. 31, 1996, now Pat. No. 5,958,974.

(51) Int. Cl.$^7$ .................................................. A67K 31/225
(52) U.S. Cl. ........................................... 514/547; 514/548
(58) Field of Search ..................................... 514/547, 548

(56) References Cited

U.S. PATENT DOCUMENTS 2,236,516    11/1941   Cahn et al. .
3,443,965    5/1969    Birnbaum et al. .
3,978,099    8/1976    Tuma et al. .
4,002,775    1/1977    Kabara .
4,446,165    5/1984    Roberts .
4,497,800    2/1985    Larson et al. .
5,560,904    10/1996   Laugier et al. .

FOREIGN PATENT DOCUMENTS

WO/95/31956    11/1995    (WO) .

OTHER PUBLICATIONS

Kabara, J., "The Pharmacological Effects of Lipids," ed. 1987, Nutritional Biochemistry, vol. 6, Jul. 1995.
Isaacs, et al., "Antimicrobial Activity of Lipids Added to Human Milk, Infant Formula, and Bovine Milk," Nutritional Biochemistry, 1995.
Larssen, et al. eds., "Food Emulsions," Publ. Marcel Dekker, Inc., 1990, Appendix Tables, pp. 2198–2247.
Danisco Ingred. USA, page from catalog titled Diacetyl Tartaric Acid Esters (DATEM) and bearing a facsimile date of Jun. 14, 1996.
Geelen, et al., "The Cell Wall Mediates Pneumococcal Attachment to and Cytopathology in Human Endothelial Cell," Infection and Immunity, vol. 61, No. 4, Apr. 1993, pp. 1538–1543.
Cundell, et al., "Relationship Between Colonial Morphology and Adherence of *Streptococcus pneumoniae*," Infection and Immunity, vol. 63, No. 3, Mar. 1995, pp. 757–761.
Stauffer, C., "Fats and Oils,"Eagan Press, May 13, 1996, pp. 42–43.
Chem. Abstracts, 123:168286–JP 078 123956/1995.

*Primary Examiner*—Zohreh Fay
(74) *Attorney, Agent, or Firm*—J. Michael Dixon

(57) ABSTRACT

A nutritional formulation containing bactericidal amounts of diacetyltartaric acid esters of mono- and diglycerides is provided. A process of inhibiting bacterial infections including the step of feeding the nutritional composition to a subject is also provided.

25 Claims, No Drawings

NUTRITIONAL FORMULATIONS CONTAINING WATER-MISCIBLE LIPID DERIVATIVES AS ANTIBACTERIAL AGENTS

CROSS REFERENCE TO RELATED APPLICATIONS

This application is a continuation of Ser. No. 09/306,608, filed on Apr. 16, 1999, now U.S. Pat. No. 6,066,669 which is a continuation of Ser. No. 08/690,737 filed Jun. 31, 1996 now U.S. Pat. No. 5,958,974.

The present application is related to "Water-Miscible Of Mono- And Diglycerides Having Antimicrobial Activity And Their Use In Inhibiting Infection," "Nutritional Formulations Containing Water-Miscible Lipid Derivatives As Antimicrobial Agents," "Water-Miscible Esters Of Monoglycerides Having Antimicrobial Activity," and "Water-Miscible Esters Of Mono-And Diglycerides Having Antibacterial Activity And Their Use In Inhibiting Infection," all of which are filed concurrently herewith, and the text of all of which are herein incorporated by reference.

TECHNICAL FIELD OF THE INVENTION

The present invention relates generally to the composition of nutritional products containing water-miscible lipid derivatives of mono- and diglycerides and fatty acids as antibacterial agents, and to the process of formulating these antibacterial agents in various nutritional matrices.

BACKGROUND OF THE INVENTION

It has been previously reported (Kabara, *The Pharmacological Effects of Lipids*, ed. 1987, and *Nutritional Biochemistry*, Vol. 6, July, 1995) that certain lipids have antimicrobial effects. Those lipids reported to have antiviral and antibacterial activity are highly lipophilic, have HLB values of 2 to 4 and likely act by affecting the infectious organism's lipid envelope or membrane leading to changes in the organism's permeability resulting in loss of infectivity.

The high lipophilicity of those lipids, however, makes it difficult to carry out prophylactic studies because the lipids are insoluble in aqueous solutions. The solubility problems can be overcome to some extent through the use of non-aqueous solvents such as ethanol or dimethylsulfoxide (DMSO) (Isaacs, Litov, and Thormar, *Nutritional Biochemistry*, 1995). Such solvents, in many instances, are inappropriate for use in humans or animals. By way of example, ethanol and DMSO are contraindicated for use in infants.

Still another problem associated with the use of existing antimicrobial lipids is that the antimicrobial action is inhibited or greatly reduced in the presence of proteins (Kabara, *The Pharmacological Effects of Lipids*, ed. 1987; and U.S. Pat. No. 4,002,775, *Fatty Acids and Derivatives as Antimicrobial Agents*, 1977). Thus, such lipids cannot be administered together with proteins such as are present in enteral nutritional formulations. There continues to be a need in the art therefore for antibacterial lipids that are soluble in aqueous formulations and those whose antibacterial activity is not adversely affected by the presence of intact protein.

BRIEF SUMMARY OF THE INVENTION

The present invention provides a nutritional formulation that contains a bactericidal amount of water-miscible lipid derivatives. Preferred water-miscible lipid derivatives are diacetyltartaric acid esters of mono- and diglycerides. The diacetyltartaric acid esters of mono- and diglycerides can be those used as GRAS emulsifiers and known as DATEMs or can be novel such esters wherein 90% or more of the fatty acid content is accounted for by a single fatty acid. Where the latter form of diacetyltartaric acid esters of mono- and diglycerides are used, the fatty acid component preferably contains from 8 to 24 and, more preferably from about 10 to about 20 carbon atoms. The fatty acid can be saturated, unsaturated or hydroxylated.

The present invention further provides a process of inhibiting a bacterial infection in a subject in need of such treatment. In accordance with that process the subject is fed an effective antibacterial amount of a nutritional formulation containing diacetyltartaric acid esters of mono- and diglycerides.

DETAILED DESCRIPTION OF THE INVENTION

I. Nutritional Formulation

The present invention provides a nutritional formulation that contains effective antibacterial amounts of water-miscible lipid derivatives. The water-miscible lipid derivative comprises a lipophilic moiety linked via an ester or ether linkage to a hydrophilic moiety. The lipophilic moiety comprises a fatty acid, a monoacylglycerol (monoglyceride), a diacylglycerol (diglyceride) derivative, a monoetherglycerol derivative, or a dietherglycerol derivative. The hydrophilic moiety comprises an organic acid, an organic alcohol or a salt thereof.

In one embodiment, the water-miscible lipid derivative is a mono-/diglyceride wherein one or two of the glycerol carbon atoms are linked to an alkyl or acyl group and at least one of the remaining glycerol carbon atoms is linked via an ester linkage to an organic acid. In a preferred embodiment, the organic acid is tartaric acid that has been derivatized with acetyl groups. In accordance with this embodiment, the water-miscible lipid derivatives are diacetyltartaric acid esters of mono- and diglycerides.

Certain of such diacetyltartaric acid esters of mono- and diglycerides are known in the art as DATEMs and are GRAS emulsifiers for foodstuffs. DATEMs are formed by reacting diacetyltartaric anhydride with partial glycerides of edible oils, fats or fat-forming fatty acids. Sources of glycerides for the production of DATEMs include soy oil, palm oil, sunflower oil, beef tallow and monoglycerides. DATEMs can also be obtained from commercial sources. For example, DATEM SOY, Panodan FDP Kosher (derived from fully hydrogenated soybean oil) DATEM SUNF, SDK (derived from unhydrogenated sunflower oil), DATEM-C12 (derived from 90% $C_{12}$ monoglyceride) and DATEM-C08 (derived from 90% $C_8$ monoglyceride), are commercially available from Danisco Ingredients, Grinsted Division.

In another embodiment, the water-miscible lipid derivative corresponds to Formula I, below.

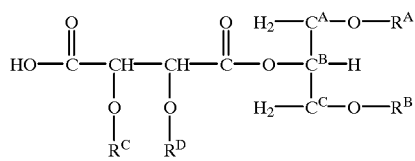

In formula I, each of $R^A$ and $R^B$ can independently be hydrogen, an acyl group having from 6 to 26 carbon atoms ($C_6$–$C_{26}$ acyl), an alkyl group having from 6 to 26 carbon atoms ($C_6$–$C_{26}$ alkyl), or an inorganic anion. Exemplary such anions are halides, nitrates, sulfates and phosphates. The acyl and alkyl groups can be saturated, unsaturated or hydroxylated. Preferably, the acyl and alkyl groups have from 8 to 24 carbon atoms and, more preferably from 10 to 20 carbon atoms. $R^A$ and $R^B$ can link to any of the $C^A$, $C^B$ or $C^C$ carbons of the glycerol backbone. Similarly, the organic acid moiety (shown as tartaric acid in Formula I) can link to any of the $C^A$, $C^B$ or $C^C$ carbons not linked to an acyl or alkyl group. One of ordinary skill in the art will recognize that other organic acids can be used in place of tartaric acid Each of $R^C$ and $R^D$ can independently be an acyl or an alkyl group containing from 2 to 6 carbon atoms, which groups can be saturated, unsaturated or hydroxylated. Exemplary $R^C$ and $R^D$ groups are acetyl and succinyl esters. In a compound of Formula I, 90% or more of the total fatty acid content is in the form a single fatty acid.

Where only one of $R^A$ or $R^B$ is an acyl group, the molecule is a monoacylglycerol (or monoglyceride) derivative. Where both of $R^A$ and $R^B$ are acyl groups, the molecule is a diacylglycerol (or diglyceride) derivative. Where only one of $R^A$ or $R^B$ is an alkyl group, it is a monoetherglycerol derivative, and if both $R^A$ and $R^B$ are alkyl groups, it is a dietherglycerol derivative. It is possible that the $R^A$ and $R^B$ can be one acyl group and one alkyl group. The linkage for the acyl group to the glycerol backbone is an ester lage, and the lage for the alkyl group to the glycerol backbone is an ether linkage.

In a preferred embodiment of Formula I, $R^A$ is a $C_8$–$C_{24}$ acyl, $R^B$ is hydrogen, $R^C$ and $R^D$ are both acetyl and the lipids are diacetyltartaric acid esters of monoglycerides.

As used herein, the term "DATEM" will be used to mean those lipids known in the art as GRAS emulsifiers and which lipids have been approved as emulsifiers by the FDA and the EEC. These DATEMs are characterized by containing a mixture of fatty acids. As used herein, the phrase "diacetyltartaric acid esters of mono- and diglycerides" means DATEMs as well as novel lipids as defined above by Formula I.

Diacetyltartaric acid esters of mono- and diglycerides are made using standard techniques well known in the art (See, e.g., Schuster and Adams, Rev. Fr. Corps Gras, 29(9) :357–365, 1981). Diacetyltartaric acid esters of mono- and diglycerides, produced either from glycerides of edible fats or from fatty acids can exist in a variety of isomer forms (See, e.g., Food Emulsions, Second Edition, Revised and Expanded, ed. by Larsson and Friberg, Marcel Dekker, Inc., New York, 1990). Thus, a lipid of Formula I can exist in different isomeric forms.

In another embodiment, the water-miscible lipid is a modified glyceride such as a fatty acid acyl lactylate or a salt thereof. Particular such lactylates (e.g., sodium stearoyl-2-lactylate) are well known GRAS emulsifiers, stabilizers and dough conditioners. The fatty acid component of the lactylate can be any fatty acid and is not limited to stearic acid. A preferred fatty acid component of a lactylate is lauric acid. Fatty acid acyl lactylates can be made using standard procedures well known in the art (See, e.g., U.S. Pat. No. 4,146,548, the disclosure of which is incorporated herein by reference).

A nutritional formulation of the present invention contains edible macronutrients, vitamins and minerals in amounts desired for a particular use. The amounts of such ingredients will vary depending on whether the formulation is intended for use with normal, healthy infants, children, or adults or subjects having specialized needs such as accompany certain pathological conditions (e.g., metabolic disorders). It will be understood by persons skilled in the art that the components utilized in a nutritional formulation of the present invention are of semi-purified or purified origin. By semi-purified or purified is meant a material which has been prepared by purification of a natural material or by synthesis. These techniques are well known in the art (See. e.g., Code of Federal Regulations for Food Ingredients and Food Processing; Recommended Dietary Allowances, 10th Ed., National Academy Press, Washington D.C., 1989).

In a preferred embodiment, a nutritional formulation of the present invention is an infant enteral nutritional product. Accordingly in a further aspect of the invention, a nutritional formulation is provided that is suitable for feeding infants. The formula comprises, in addition to diacetyltartaric acid esters of mono- and diglycerides, macronutrients, vitamins and minerals in amounts designed to provide the daily nutritional requirements of infants. It is important to note that antimicrobial factors in human milk or in infant formulas, may reach an infant's respiratory tract directly as a result of regurgitation and inhalation of these factors during and after feeding. The mucosa of the respiratory tract may gain direct protection in this way.

The macronutritional components include edible fats, carbohydrates and proteins. Exemplary edible fats are coconut oil, soy oil, and mono- and diglycerides. Exemplary carbohydrates are glucose, edible lactose and hydrolyzed cornstarch Atypical protein source would be soy protein, electrodialysed whey or electrodialysed skim milk or milk whey, or the hydrolysates of these proteins, although other protein sources are also available and may be used. These macronutrients would be added in the form of commonly accepted nutritional compounds in amount equivalent to those present in human milk on an energy basis, i.e., on a per calorie basis.

The infant formula would preferably include the following vitamins and minerals: calcium, phosphorous, potassium, sodium, chloride, magnesium, manganese, iron, copper, zinc, selenium, iodine, and Vitamins A, E, D, C, and the B complex.

The infant formula can be sterilized and subsequently utilized on a ready-to-feed (RTF) basis or stored in a concentrated liquid or a powder. The powder can be prepared by spray drying the infant formula prepared as indicated above, and the formula can be reconstituted by rehydrating the concentrate. Infant nutritional formulas are well known in the art and commercially available (e.g., Similac® and Alimentum® from Ross Products Division, Abbott Laboratories).

Actual dosage levels of diacetyltartaric acid esters of mono- and diglycerides ingredients in the compositions of the present invention may be varied so as to obtain an amount of active ingredient that is effective to obtain a desired prophylactic response for a particular composition and method of administration. The selected dosage level therefore depends upon the desired therapeutic effect, on the route of administration, and on the desired duration of administration and other factors.

In a preferred embodiment, where the water-miscible esterified derivative is a diacetyltartaric acid ester of mono- and diglycerides, an effective anti-bacterial amount for use in a nutritional formulation is from about 1,000 to about 5,000 milligrams per liter (micrograms per milliliter). Where the nutritional formulation contains intact protein, a more preferred level is from about 2,000 to about 4,000 milligrams per liter. Where the nutritional formulation contains protein hydrolysates such as casein, an effective anti-bacterial concentration is from about 1,500 to about 3,000 milligrams per liter. Preferably, the amount of water-miscible esterified mono- and diglyceride derivative should be equal to or less than 10% of the total fat present in the nutritional composition. More preferably, the water-miscible derivative should account for no less than about 6% of the total fat. Where the nutritional formulation contains protein, the weight ratio of water-miscible lipid to protein is equal to or greater than about 1:4.2.

II. Process of Inhibiting Bacterial Infection

In another aspect, the present invention provides a process of inhibiting a bacterial infection in a subject in need of such treatment. In accordance with that process, the subject is fed a nutritional composition of the present invention Preferred such compositions are the same as set forth above. A preferred subject is a human infant As disclosed herein, a formulation of the present invention can be used to inhibit bacterial infections. As used herein, the term "inhibit" means treat or prevent. The nutritional formulation is particularly effective in inhibiting bacterial infections of the upper gastrointestinal tract, the respiratory tract or the ear. As used herein the term "upper gastrointestinal tract" means the mouth, throat, esophagus, stomach and duodenum. As used herein the term "respiratory tract" means the nose, sinuses, eustachian tube, middle ear, mouth, throat, trachea and other airways and the lung (including the alveoli). A process of the present invention has particular utility in inhibiting bacterial infections of the nose, mouth, sinuses, throat, middle ear, stomach and lung.

Diacetyltartaric acid esters of mono- and diglycerides are effective bactericides against infections caused by a wide range of bacteria, including gram-positive and gram-negative bacteria Exemplary such bacteria are members of the genus Streptococcus, Haemophilus, Helicobacter, Staphylococcus, Enterococcus, Micrococcus, Enterobacter, Klebsiella, Providensia, Pseudomonas, Acinetobacter, Candida, Mycobacterium, Nocardia, and Eschericia. Exemplary particular bacteria are *S. aureus, S. epidermis, S. bovis, S. agalactiae, S. pyogenes, M. luteus, P. aeruginosa, M. smegmatis, N. asteroides, S. pneumoniae, H. influenzae,* and *H. pylori.*

*Streptococcus pneumoniae* (*S. pneumoniae*) is a gram-positive coccus that usually initiates infection by colonization of the nasopharynx followed by aerosolized spread to the respiratory tract. Clinical manifestations include localized and systemic infections including otitis media, pneumonia, sepsis and meningitis (Geelen, Bhattacharyya, and Tuomanen, *Infection and Immunity,* 1993; Cundell, Weiser, Shen, Young, and Tuomanen, *Infection and Immunity,* 1995). Additionally, S. pneumoniae is the single most frequent cause of otitis media (OM), a common and significant illness in infants and children that accounts for more than one third of office visits to pediatricians (Thoene and Johnson, 1991; Kaleida, Nativio, Chao, and Cowden, *Jr. of Clinical Microbiology,* 1993). *Haemophilus influenzae* (*H. influenzae*) is another common bacterial agent known to cause otitis media in infants and young children. *Helicobacter pylori* (*H. pylon*) is a microaerophilic gram-negative bacterium that infects 50% of the population at age 60 in the US (Blaser, Clinical Infectious Diseases, 1992), and 90% of children by age 5 in the developing countries (Thomas et al., Lancet, 1992). *H. pylori* is a major cause of gastritis, plays a key role in the etiology of peptic ulcer and is a risk factor for gastric cancer.

The following examples illustrate preferred embodiments of the present invention and are not limiting of the claims and specification in any way.

EXAMPLE 1

Bactericidal Effects of Diacetyltartaric Acid Esters of Mono- and Diglycerides on *S. pneumoniae*

Bactericidal Assay

*Streptococcus pneumoniae* (*S. pneumoniae*) (strain 6303, American Type Culture Collection, Rockville, Md.) was cultured overnight on TSA II (with 5% Sheep Blood) agar plates and harvested at approximately 18 hours using 10 ml of sterile Dulbecco's Phosphate buffered saline (D-PBS). The bacterial suspension was centrifuged at 2000 RPM for 15 minutes at room temperature. The supernatant was discarded and the pellet re-suspended in 2 ml of sterile D-PBS. The re-suspended bacterial suspension was pipetted into two sterile microcentrige vials and centriged for 4 minutes using an Eppendorf microcentrifuge (8800×g). The supernatant was discarded and the bacterial pellet was resuspended in 2 ml of sterile PBS.

The bacterial count was typically 109 colony forming units (CFU)/ml. 180 $\mu$l of each test product or control was added to sterile microcentifuge vials followed by 20 $\mu$l of the *S. pneumoniae* suspension (9 parts infant formula: 1 part bacterial suspension). Each vial was mixed and incubated for 1 hour at 37° C. 100 $\mu$l of each test product was then plated on TSA II agar and the inoculum spread over the agar surface.

The inoculum was quantitated by serially diluting the initial bacterial suspension to a final dilution of $10^{-4}$, $10^{-5}$, $10^{-6}$, $10^{-7}$, and $10^{-8}$ and plated on TSA II agar. The plates were then inverted and incubated at 37° C./$CO_2$ 5% incubator for 18 to 24 hours. Growth of bacteria was recorded as growth versus no growth for each of the variables. In some assays, the formula-bacterial suspension ratio was changed to 6.6 parts infant formula to 3.3 parts bacterial suspension changing the final protein concentration in the assay from 13.5 to 9.9 mg/mL.

Test Agents

Monoglyceride C12:0 was obtained from Grinsted Division of Danisco containing a minimum of 90%o monoester of C12:0. DATEM SOY, Panodan FDP Kosher was obtained from Danisco Ingredients, Grinsted Division. It is derived from fully hydrogenated soybean oil (U.S. DATEM SPECIFICATIONS). DATEM SUNF, SDK was obtained from Danisco Ingredients, Grinsted Division. SDK is derived from unhydrogenated sunflower oil (U.S. DATEM SPECIFICATIONS). DATEM-C12 was obtained from Danisco Ingredients and is derived from 90% $C_{12}$ monoglyceride. DAI-C08 was obtained from Danisco Ingredients and is derived from 90% $C_8$ monoglyceride which was obtained from Hullis America.

The results of these studies are summarized below in Tables 1 and 2.

TABLE 1

S. PNEUMONIAE BACTERICIDAL ASSAY IN DILUTE INFANT FORMULA (9.9 MG PROTEIN/ML)

| TREATMENT | FINAL CONCENTRATION OF DATEM in $\mu$g/ml | LOG REDUCTION[a] |
|---|---|---|
| INFANT FORMULA CONTROL | 0 | 0 |
| DATEM SUNF | 2400 | 4.3 |
| DATEM-C12 | 2400 | 4.9 |
| DATEM-C08 | 2400 | 2.4 |

[a]Log reduction is the reduction of bacteria titer in $\log_{10}$. The *S. pneumoniae* inoculum was 4.9 $\log_{10}$.

TABLE 2

S. PNEUMONIAE BACTERICIDAL ASSAY IN INFANT FORMULA (13.5 MG PROTEIN/ML)

| TREATMENT | FINAL CONCENTRATION OF DATEM in µg/ml | LOG REDUCTION |
|---|---|---|
| INFANT FORMULA CONTROL | 0 | 0 |
| DATEM SOY | 3300 | 0 |
| DATEM SUNF | 3300 | 0 |
| DATEM C12 | 3300 | 6.8 |
| DATEM-C08 | 3300 | 0 |
| $C_{12}$ MONO-GLYCERIDE | 4500 | 0 |

The S. pneumoniae inoculum was 6.8 $log_{10}$.

The data from Tables 1 and 2 show that diacetyltartaric acid esters of mono- and diglycerides are effective as a S. pneumoniae bactericidal agents in an aqueous enteral formulation The data also show that the bactericidal action of diacetyltartaric acid esters of mono- and diglycerides is not adversely affected by the presence of protein. Each of the diacetyltartaric acid esters of mono- and diglycerides tested at lower protein concentrations (9.9 mg/ml) had significant bactericidal activity versus S. pneumoniae. Only DATEM-C12 produced from $C_{12}$ monoglyceride demonstrated bactericidal activity at protein concentrations normally found in infant formula at an inoculum of 6.8 $log_{10}$.

Animal Studies

Neonatal (24 hours-old) rats (10 rats per group) were inoculated with various test samples containing one of two strains of S. pneumoniae (Sp DB31 and Sp DB40 at 5.72 and 4.74 $log_{10}$ inoculum dose, respectively). These mixtures were incubated at 37° C. for one hour before intranasal inoculation. Nasopharyngeal lavage fluid of the rat was collected 24 hours after S. pneumoniae inoculation and analyzed for S. pneumoniae population. Three different test samples were studied: Similac® RTF alone as a control; DATEM-C12 added to the basic control at 3650 mg/L, and DATEM-C12 (1825 mg/L) and sunflower monoglyceride (5000 mg/L). The results from these animal studies are summarized below in Table 3.

TABLE 3

DATEM INHIBITS S. PNEUMONIAE INFECTION IN NEONATAL RATS

| Treatment | Sp strain DB31 $Log_{10}$ CFU/ml | Sp strain DB40 |
|---|---|---|
| SIM RTF (Control) | 5.75 ± 0.10 | 6.29 ± 0.26 |
| DATEM-C12 (3650 ppm) | 3.75 ± 0.94 | 2.57 ± 0.70 |
| DATEM-C12 + MG (1825 ppm + 500 ppm) | 0.00 ± 0.00 | 0.66 ± 0.45 |

The data from Table 3 show that diacetyltartaric acid esters of mono- and diglycerides alone are effective in suppressing S. pneumoniae infection in vivo and that the combination of DATEM-C12 and monoglyceride provided the greatest bactericidal activity.

EXAMPLE 2
Bactericidal Effects of Diacetyltartaric Acid Esters of Mono- and Diglycerides on *Haemophilus Influenzae*

The bactericidal effects of diacetyltartaric acid esters of mono- and diglycerides against H. influenzae was determined in vitro using the procedures set forth above in Example 1. The results of these studies are summarized below in Table 4.

TABLE 4

DATEM-C12 INHIBITS H. INFLUENZAE GROWTH

| Treatment | Concentration (µg/ml) | $Log_{10}$ Count/Reduction | Temperature |
|---|---|---|---|
| 66% Similac ® RTF | 0 | 6.8/no reduction | 37° C. |
| DATEM-C12 | 2400 | 0/6.8 log reduction | 37° C. |
| DATEM-C12 + C12 MG | 1200/3300 | 0/6.8 log reduction | 37° C. |
| DATEM-C12 + C12 MG | 1200/3300 | 0/6.8 no reduction | 22° C. |

The data in Table 4 show that diacetyltartaric acid esters of mono- and diglycendes are effective bactericidal agents against H. influenzae. In addition, when a 90% Similac® RTF formula was used, diacetyltartaric acid esters of mono- and diglycerides were found to be inactive against H. influenzae.

EXAMPLE 3
Bactericidal Effects of Diacetyltartaric Acid Esters of Mono- and Diglycerides on *Helicobacter pylori*

The bactericidal effects of diacetyltararic acid esters of mono- and diglycerides on H. pylori were studied in vitro using the procedure as described below.

MIC, minimum inhibitory concentration, was determined by adding a series of concentrations of the test compound to the H. pylori culture medium. After a 5 day incubation period at 37° C., H. pylori growth was judged by opacity of the culture medium. When 50% Similac® was used, the MIC could not be determined MUBC, minimum bactericidal concentration, was determined by adding test compound to H. pylori medium and incubating at 37° C. for 4 hours. An aliquot of the mixture was plated in H. pylori culture media. The end point was bacterial growth.

The results of these studies are summarized below in Table 5.

TABLE 5

THE MIC AND MBC OF DATEM-C12 AGAINST H. PYLORI

| Organism | MIC/MBC Broth[a] (µg/ml) | MIC/MBC in 50% Similac[b] (µg/ml) | Similac ® only (% dilution) |
|---|---|---|---|
| H. pylori 2597 | 19.5/39.1 | ND*/19.5 | 25%, no inhibition |
| | | | 50%, slight inhibition |
| H. pylori 3921 | 78.1/78.1 | ND*/78.1 | 50%, no inhibition |

ND = not done.
[a,b]MIC, minimum inhibitory concentration; MBC, minimum bactericidal concentration. Because MIC is judged by clearness of the culture medium, MIC cannot be judged in 50% Similac ®. The MBC can be determined because a liquid of the mixture is plated in culture media and the end point is bacterial growth.

The data in Table 5 show that DATEM-C12's MIC (minimum inhibitory concentration) and MBC (minimum bactericidal concentration) in the bacterial culture medium and in Similac® indicate that diacetyltartaric acid esters of mono- and diglycerides are strong compounds in inhibiting H. pylori. The data also show that Similac® does not affect DATEM-C12's bactericidal activity against H. pylori.

EXAMPLE 4
Inhibition of Respiratory Syncytial Virus Infection in HEp-2 Cells HEp-2, human laryngeal epidermal carcinoma cells were obtained from the American Type Culture Collection (Rockville, Md.). HEp-2 cells seeded at a density of 10,000 cells per well in a 96 well plate (Costar, Cambridge, Mass.) were cultured in Dulbecco's Modified Eagle's (DME) medium supplemented with 10% fetal bovine serum (FBS). The HEp-2 plates were incubated for two days at 37° C. in a humidified incubator in a 5% $CO_2$:95% air atmosphere until the monolayers were confluent. RSV stock and test sample prepared at two times their desired final concentrations were pre-mixed at equal volumes and incubated for 1 hour at 2–8° C. Virus stock was prepared to yield approximately 90% cell death in control wells which contained no virus inhibitors. 100 μl of virus/test sample mixture were added to wells containing BEp-2 monolayers previously washed in serum free minimal essential medium. The pre-incubation mixture was allowed to absorb onto the cell monolayer for two hours and then removed and replaced with serum-free minimal essential medium. The cell/virus plates were incubated at 37° C. for 4 days before quantification of virus induced cytopathic effect.

Cell survival, quantified spectrophotometrically in each well, was determined by adding 100 μl of a 20% solution of Alamar Blue dye over the virus inoculum. Alamar Blue dye measures the metabolic activity of living cells employing an oxidation/reduction color indicator that measures metabolic reduction of the growth medium. Cell metabolic activity is indicated by a color change from blue to red. Plates incubated for 4 hours at 37° C. were read on a Molecular Devices (Menlo Park, Calif.) plate reader using a dual endpoint format at 570 nm subtracting the 600 nm wavelength. The percent cell survival correlates directly to the percent virus inhibition by the sample. The percent cell survival in each well was calculated based upon the no virus cell control. Each sample was tested using replicates of four wells. Control wells containing no test agent with and without virus were completed in replicates of eight wells Test Agents Monoglyceride of unhydrogenated sunflower oil was obtained from Eastman Chemical as Myverol 18-92 distilled glycerol monolinoleate containing, by assay, 90% monoester derived from sunflower oil with a fatty acid distribution of 7.0% glycerol monopalmitate, C16:0; 4.5% glycerol monostereate, C18:0; 18.7% glycerol monooleate, C18:1; 67.5% glycerol monolinoleate, C18:2. Monoglyceride C12:0, was obtained from Grinsted Division of Danisco containing a minimum of 90%o monoester of C12:0. DATEM SOY, Panodan FDP Kosher was obtained from Danisco Ingredients, Grinsted Division. It is derived from fully hydrogenated soybean oil (U.S. DATEM SPECIFICATIONS). DATEM PALM, Myvatem 35, was obtained from Eastman Chemical Co. It is derived from fully hydrogenated palm oil (U.S. DATEM SPECIFICATIONS). DATEM SUNF, SDK was obtained from Danisco Ingredients, Grinsted Division. SDK is derived from unhydrogenated sunflower oil (U.S. DATEM SPECIFICATIONS). DATEM BEEF was obtained from Henkel Corp. and is derived from fully hydrogenated beef tallow (EUROPEAN DATEM SPECIFICATIONS). DATEM-C12 was obtained from Danisco Ingredients and is derived from 90% $C_{12}$ monoglyceride. DATEM-C08 was obtained from Danisco Ingredients and is derived from 90% $C_8$ monoglyceride which was obtained from Hullis America.

The various test agents were prepared by adding the test compound to various forms of an infant nutritional product (Similac®). The samples were hand shaken and then retorted utilizing a Steritort continuous sterilizer simulator (FMC, Princeton, N.J.) at a minimum product temperature of 258° F. and $F_o$ greater than or equal to 6. The Steritort system utilizes a gradient water preheat, followed by a saturated steam cook, and a gradient water cool. All cycles were continuously agitated. Carrageenan (previously found to contain anti-RSV activity) was removed from the formulation to allow testing of the agents. The pre-incubation mixture was allowed to absorb onto the cell monolayer for two hours and then removed and replaced with serum-free minimal essential medium. The results of these cell culture studies are summarized below in Table 6.

TABLE 6

INHIBITION OF RSV BY LIPID AGENTS IN INFANT FORMULA MATRIX (SIMILAC ® )

| TEST AGENT | CONCENTRATION (μg/ml) | PERCENT INHIBITION |
|---|---|---|
| DATEM SOY | 1825 | 98 |
|  | 608 | 0 |
|  | 203 | −17 |
|  | 68 | −13 |
|  | 23 | −12 |
|  | 7.4 | −12 |
| DATEM PALM | 1825 | 84 |
|  | 912 | 36 |
|  | 456 | 11 |
|  | 228 | 1 |
|  | 114 | 2 |
|  | 57 | 10 |
| DATEM SUNF | 1825 | 99 |
|  | 912 | 100 |
|  | 456 | 34 |
|  | 228 | 5 |
|  | 114 | −8 |
|  | 57 | −3 |
| DATEM BEEF | 1825 | 100 |
|  | 912 | 100 |
|  | 456 | 52 |
|  | 228 | −3 |
|  | 114 | −5 |
|  | 57 | 0 |
| DATEM-C12 | 1825 | 99 |
|  | 912 | 100 |
|  | 456 | 42 |
|  | 228 | −9 |
|  | 114 | −8 |
|  | 57 | −13 |
| DATEM-C08 | 1825 | 78 |
|  | 912 | −14 |
|  | 456 | −6 |
|  | 228 | −6 |
|  | 114 | −4 |
|  | 57 | −5 |
| $C_{18}$ MONOGLYCERIDE* | 229 | −8 |
|  | 115 | −13 |
|  | 57 | −18 |
|  | 29 | −21 |
|  | 0 | −22 |
| MONOGLYCERIDE $C_{12}$ | 1000 | 96 |
|  | 500 | 42 |
|  | 250 | 2 |
|  | 125 | −18 |
|  | 63 | −16 |

*Monoglyceride C18:0 mixed with equal weight of soy fatty acid to aid in solubility. The listed concentration is that of monoglyceride only.

The data in Table 6 were obtained using a 1:1 mixture of infant formula and virus in diluted cell culture medium. These data show that diacetyltartaric acid esters of mono- and diglycerides have significant anti-RSV activity in an infant nutritional formula that contains protein. To assure that anti-RSV activity would not disappear in full strength infant formula, additional studies were performed whereby the virus was diluted directly in to infant formula in place of cell culture medium and the virus neutralization assay performed as described above. All diacetyltartaric acid esters of mono- and diglycerides, with the exception of those derived from $C_8$ monoglyceride, retained activity in infant formula.

To compare the anti-RSV activity of different forms of diacetyltartaric acid esters of mono- and diglycerides, the DATEM suppliers were asked to make 4 forms of diacetyltartaric acid esters of mono- and diglycerides differing in the length and saturation of fatty acid chains by using different oils. These diacetyltartaric acid esters of mono- and diglycerides forms were: DATEM-C12:0, DATEM-PALM OIL, DATEM-SUNFLOWER OIL and DATEM-SOY. The forms of diacetyltartaric acid esters of mono- and diglycerides were mixed individually into Similac® and the activity against RSV infectivity was determined as described above. The results of these studies are summarized in Table 7 below.

TABLE 7

DIFFERENT FORMS OF DATEM ON RSV INFECTIVITY IN SIMILAC ®

| Forms of DATEM | $IC_{50}$ in Similac ® (μg/ml) |
|---|---|
| DATEM-C12:0 | 450 |
| DATEM-Soy (C18:0/C16:0) | 110 |
| DATEM-Sunflower (C18:2) | 540 |
| DATEM-Palm (C16:0) | 1120 |

The data in Table 7 show that diacetyltartaric acid esters of mono- and diglycerides made from the different fats all have inhibitory activity against RSV infection in infant formula

EXAMPLE 5

In vivo Prevention of RSV Infection in Cotton. Rats

Cotton rats have been used as an RSV research animal model for about 20 years. The cotton rat has a similar pathological change in the lung to that observed in human infants when infected by RSV (Prince et al., 1978). Also, RSV vaccine-treated cotton rats develop severe histological damage when exposed to RSV, which is similar to what occurs in human infants (Prince et al., 1986). It has also been observed that the intravenously-administered RSV-IgG has to reach a titer of ≧1:100 concentration to show the preventive effect (Prince et al., 1985). The same serum concentration of RSV-IgG in human infants is protective (Groothuis et al., 1993, 1995). Due to these similarities, the FDA has recommended the cotton rat as an appropriate model for RSV studies.

To have a repeatable RSV nasal and lung infection, a high RSV dose ($10^4$ pfu/animal) was intra-nasally inoculated to all animals. The inoculum (100 μl) consisted of 50 μl of RSV stock solution and 50 μl of test product. The test products, diacetyltartaric acid esters of mono- and diglycerides, monoglyceride (MG) and carrageenan, were suspended respectively in an infant formula that did not contain carrageenan, soy lecithin, or Myverol (a modified Similac®, or M. Similac®). In addition, some studies were performed in an infant formula in which the intact protein was replaced with a casein hydrolysate (Alimentum®). All animals consumed the regular rodent chow diet throughout the experimental period. Four days after RSV challenge, all animals were sacrificed. Their lung and nasal tissue were isolated for determination of RSV titers. As a positive control, a 5% RSV-IgG was always used. A negative control group (without any treatment before and after RSV challenge) was also employed for each experiment RSV titers in the lung and nasal tissues from the negative control group must be at the regular high level to validate the data Also, a very low RSV titer in the lung and nasal tissues from the positive control group was used to validate the experiment data. The results of these studies are summarized in Table 8 below.

TABLE 8

DATEM (C18:0/C16:0) INHIBITION OF RSV INFECTION IN COTTON RATS

| Treatment | # of Rats | RSV titer in Lung (Log₁₀ PFU/g tissue) | RSV titer in Nose |
|---|---|---|---|
| Negative Control | 12 | 3.05 ± 0.28 | 4.20 ± 0.25 |
| IgG Positive Control | | 100% inhibition | 100% inhibition |
| Formula Control (M. Similac ® )* | 12 | $3.22 \pm 0.19^A$ | $3.21 \pm 0.70^a$ |
| DATEM in M. Similac ® (1825 mg/L) | 12 | $3.23 \pm 0.24^A$ | $2.90 \pm 0.68^a$ |
| DATEM in M. Similac ® (3650 mg/L) | | $2.68 \pm 0.41^B$ | $2.00 \pm 0.66^b$ |
| DATEM 1825 mg/L + MG 3650 mg/L in M. Similac ® (DATEM & MG pre-mix with water) | 12 | $2.50 \pm 0.40^B$ | 100% inhibition[b] |
| DATEM 1825 mg/L + MG 3650 mg/L in M. Similac ® (DATEM & MG pre-mix with oil) | 12 | $2.69 \pm 0.41^B$ | 100% inhibition[b] |
| DATEM 1825 mg/L + MG 5000 mg/L in M. Similac ® (DATEM & MG pre-mix with water | 11 | $2.50 \pm 0.40^B$ | 100% inhibition[b] |
| DATEM in Alimentum ® Powder (1825 mg/L) | 6 | $2.72 \pm 0.31^B$ | $2.31 \pm 0.51^b$ |
| 1000 mg/L Carrageenan in M. Similac ® | 11 | $3.06 \pm 0.16^A$ | $3.78 \pm 0.47^a$ |

*This formula control was used as a base for comparison with other treatment groups. Values in a column labeled with a different superscript letter differ at $P < 0.05$.

The data from Table 8 show that diacetyltartaric acid esters of mono- and diglycerides inhibit RSV infection in vivo. The data also show that diacetyltartaric acid esters of mono- and diglycerides and MG act synergistically to inhibit-RSV activity. Pre-mixing diacetyltartaric acid esters of mono- and diglycerides and MG in water or in oil does not result in a difference in anti-RSV activity. Diacetyltartaric acid esters of mono- and diglycerides are effective virucide in infant nutritional products both in the presence (Similac®) and absence (Alimentum®) of intact protein.

What is claimed is:

1. A nutritional composition having antibacterial activity that comprises a bactericidal amount of diacetyltartaric acid esters of mono- and diglycerides and edible macronutrients.

2. The composition of claim 1 wherein the diacetyltartaric acid esters of mono- and diglycerides are obtained from soy oil, palm oil, sunflower oil, beef tallow or other edible oil sources.

3. The composition of claim 1 wherein the diacetyltartaric acid esters of mono- and diglycerides correspond to Formula I, below:

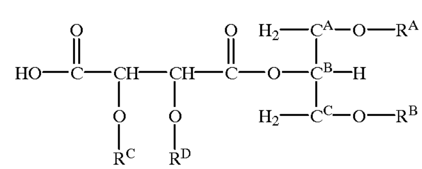

where $R^A$ is a $C_8$–$C_{24}$ fatty acid, $R^B$ is H, $R^C$ and $R^D$ are acetyl, and wherein 90% or more of the total fatty acid content is in the form of a single fatty acid.

4. The composition of claim 3 wherein $R^A$ is a $C_{10}$–$C_{20}$ fatty acid.

5. The composition of claim 3 wherein $R^A$ is a $C_{12}$–$C_{18}$ fatty acid.

6. The composition of claim 3 wherein $R^A$ is a $C_{12}$ fatty acid.

7. The composition of claim 3 wherein the $C_8$–$C_{24}$ fatty acid is saturated, unsaturated or hydroxylated.

8. The composition of claim 1 wherein the edible macronutrients are formulated for feeding to an infant.

9. The composition of claim 8 wherein the macronutrients comprise one or more of coconut oil, soy oil, mono- and diglycerides, glucose, edible lactose, electrodialysed whey and electrodialysed skim milk, milk whey, soy protein, and other protein hydrolysates.

10. The composition of claim 9 wherein the weight ratio of diacetyltartaric acid esters of mono- and diglycerides to protein (weight/weight) is greater than or equal to 1:4.2.

11. The composition of claim 1 that is in liquid form.

12. The composition of claim 1 that is in solid form.

13. The composition of claim 1 further comprising one or more of vitamins A, C, D, E and B complex.

14. The composition of claim 1 further comprising one or more of minerals calcium, magnesium, manganese, sodium, potassium, phosphorus, copper, zinc, chloride, iodine, selenium and iron.

15. A nutritional composition comprising a bactericidal amount of diacetyltartaric acid esters of mono- and diglycerides; edible macronutrients formulated for feeding to an infant and comprising one or more of coconut oil, soy oil, mono- and diglycerides, glucose, edible lactose, electrodialysed whey, electrodialysed skim milk and milk whey; one or more of vitamins A, C, D, E and B complex; and one or more of minerals calcium, magnesium, manganese, sodium, potassium, phosphorus, copper, zinc, chloride, iodine, selenium and iron.

16. The composition according to claim 1 in which said nutritional composition is a enteral nutritional formula.

17. The formula according to claim 16 in which said diacetyltartaric acid esters of mono- and diglycerides is present at a concentration of about 1000 mg to about 5000 mg per liter of formula.

18. The formula according to claim 16 in which said formula contains protein, fat and a blend of edible oils.

19. The formula according to claim 18 in which said diacetyltartaric acid esters of mono- and diglycerides is present in an amount equaling at least 6 wt % of the oil blend.

20. The formula according to 19 wherein the weight ratio of diacetyltartaric acid esters of mono- and diglycerides to protein (weight/weight) is greater than or equal to 1:4.2.

21. The formula according to claim 16 in which said diacetyltartaric acid esters of mono- and diglycerides is present at a concentration of from about 2,000 to about 4,000 mg per liter of said formula.

22. The formula according to claim 16 in which said diacetyltartaric acid esters of mono- and diglycerides is present at a concentration of from about 1,500 to about 3,000 mg per liter of said formula.

23. The formula according to claim 17 in which said diacetyltartaric acid esters of mono- and diglycerides is present in an amount of at least 3000 milligrams per liter of said formula.

24. The formula according to claim 23 in which said diacetyltartaric acid esters of mono- and diglycerides is present in an amount equaling at least 6 wt % of the total oil blend.

25. The formula according to claim 23 wherein the weight ratio of diacetyltartaric acid esters of mono- and diglycerides to protein (weight/weight) is greater than or equal to 1:4.2.

* * * * *

UNITED STATES PATENT AND TRADEMARK OFFICE
CERTIFICATE OF CORRECTION

PATENT NO. : 6,228,886 B1
DATED : May 8, 2001
INVENTOR(S) : Anderson et al.

It is certified that error appears in the above-identified patent and that said Letters Patent is hereby corrected as shown below:

Column 14, claim 18,
Claim 18 should read:

-- The formula according to claim 17 in which said formula contains protein, fat and a blend of edible oils.

Signed and Sealed this

Ninth Day of April, 2002

JAMES E. ROGAN
Director of the United States Patent and Trademark Office

Attest:

Attesting Officer